US008363891B1

(12) United States Patent
Weyand et al.

(10) Patent No.: US 8,363,891 B1
(45) Date of Patent: Jan. 29, 2013

(54) SYSTEM AND METHOD FOR PREDICTING A FORCE APPLIED TO A SURFACE BY A BODY DURING A MOVEMENT

(75) Inventors: Peter G. Weyand, Dallas, TX (US);
Kenneth P. Clark, Dallas, TX (US);
Laurence J. Ryan, Richardson, TX (US)

(73) Assignee: Southern Methodist University, Dallas, TX (US)

( * ) Notice: Subject to any disclaimer, the term of this patent is extended or adjusted under 35 U.S.C. 154(b) by 0 days.

(21) Appl. No.: 13/430,427

(22) Filed: Mar. 26, 2012

(51) Int. Cl.
*G06K 9/00* (2006.01)
(52) U.S. Cl. .......................................... 382/100
(58) Field of Classification Search .................. 382/100
See application file for complete search history.

(56) References Cited

U.S. PATENT DOCUMENTS

| | | | |
|---|---|---|---|
| 6,438,255 B1 * | 8/2002 | Lesniak | 382/107 |
| 6,916,295 B2 * | 7/2005 | Tasch et al. | 600/595 |
| 7,931,604 B2 * | 4/2011 | Even Zohar et al. | 600/595 |
| 7,969,315 B1 | 6/2011 | Ross et al. | 340/573.1 |
| 7,998,040 B2 * | 8/2011 | Kram et al. | 482/124 |
| 2007/0068244 A1 * | 3/2007 | Billing et al. | 73/172 |
| 2012/0191017 A1 * | 7/2012 | Huang | 600/595 |

OTHER PUBLICATIONS

Elsevier, Journal of Sound and Vibration, "*Reproduction and application of human bouncing and jumping forces from visual marker data*", Journal of Sound and Vibration 329 (2010) 3397-3416), journal homepage: www.elsevier.com/locate/jsvi, (20 pgs.), 2010.
M. Bobbert, H. Schamhardt, B. Nigg, "*Calculation of Vertical Ground Reaction Force Estimates During Running From Positional Data*", Human Performance Laboratory, Faculty of Physical Education, Univ. of Calgary, Canada; Journal of Biomechanics vol. 24, No. 12, pp. 1095-1105, 1991 (11 pgs.), 1991.
Customized Patient Rehabilitation—MedHab; http://www.medhab.com/ (8 pgs), copyright listed as 2010; printed Oct. 29, 2012.

* cited by examiner

*Primary Examiner* — Vikkram Bali
(74) *Attorney, Agent, or Firm* — Baker Botts L.L.P.

(57) ABSTRACT

According to one embodiment, a system includes at least one memory and at least one processor. The processor receives information that includes a position or motion of one or more points of a body during a movement. Based at least on the position or motion of the one or more points of the body during the movement, the processor calculates a first one or more curves indicative of a first force between a surface and at least a first portion of the body, and calculates a second one or more curves indicative of a second force between the surface and at least a second portion of the body. The processor further predicts a force applied to the surface by the body during the movement by combining the first and second one or more curves.

26 Claims, 8 Drawing Sheets

SYSTEM AND METHOD FOR PREDICTING A FORCE APPLIED TO A SURFACE BY A BODY DURING A MOVEMENT

TECHNICAL FIELD

This disclosure relates generally to the field of force prediction and more specifically to a system and method for predicting a force applied to a surface by a body during a movement.

BACKGROUND

Traditionally, in order to determine a force applied to a surface by a body during a movement (such as a force applied to the ground by the body of a person running), the force applied to the surface is measured by a direct force measurement system, such as a force plate, an instrumented force treadmill, and/or an insole force sensor. Unfortunately, these traditional direct force measurement systems can be impractical. In particular, such traditional direct force measurement systems are expensive and difficult to implement and maintain.

SUMMARY OF THE DISCLOSURE

According to one embodiment, a system includes at least one memory and at least one processor. The processor receives information that includes a position or motion of one or more points of a body during a movement. Based at least on the position or motion of the one or more points of the body during the movement, the processor calculates a first one or more curves indicative of a first force between a surface and at least a first portion of the body, and calculates a second one or more curves indicative of a second force between the surface and at least a second portion of the body. The processor further predicts a force applied to the surface by the body during the movement by combining the first and second one or more curves.

Certain embodiments of the disclosure may provide one or more technical advantages. For example, instead of measuring the force applied to a surface by a body, a calculation device may predict the force applied to the surface by the body. In particular embodiments, this may allow the force to be determined without having to actually measure it. As such, since measuring the force tends to be expensive, in particular embodiments, the force may be determined in a less expensive manner.

Certain embodiments of the disclosure may include none, some, or all of the above technical advantages. One or more other technical advantages may be readily apparent to one skilled in the art from the figures, descriptions, and claims included herein.

BRIEF DESCRIPTION OF THE DRAWINGS

For a more complete understanding of the present disclosure and its features and advantages, reference is now made to the following description, taken in conjunction with the accompanying drawings, in which.

DETAILED DESCRIPTION OF THE DRAWINGS

Embodiments of the present disclosure are best understood by referring to FIGS. 1 through 6 of the drawings, like numerals being used for like and corresponding parts of the various drawings.

Figure 1:
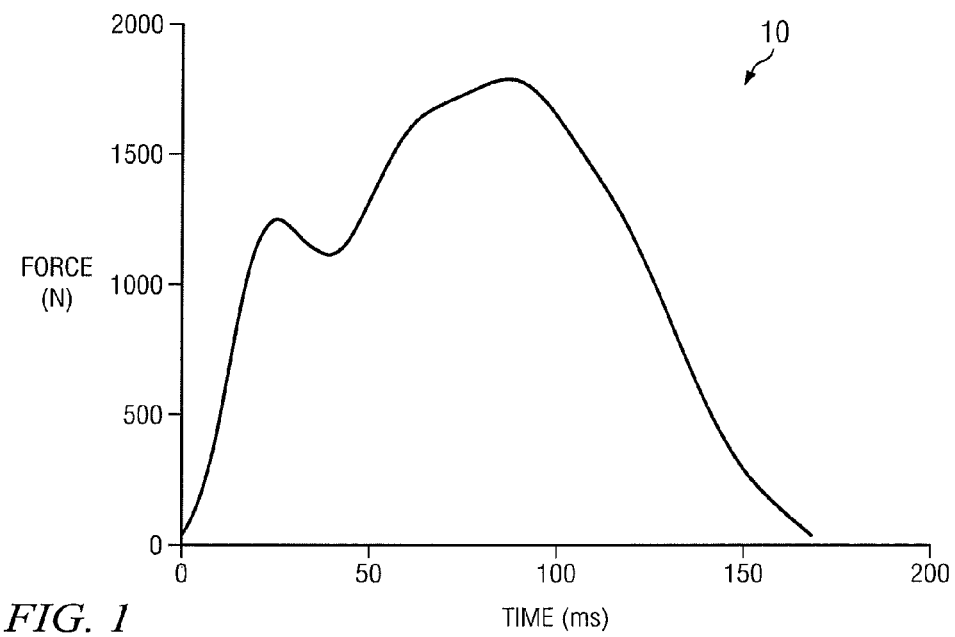
FIG. 1 illustrates an example force curve.

FIG. 1 illustrates an example force curve 10. According to the illustrated embodiment, force curve 10 illustrates the ground reaction force (GRF) that occurs when a person is running. GRF represents the force of the ground pushing on the body of the person during a step of the run, or, alternatively, the force of the body pushing on the ground during a step of the run. In particular embodiments, GRF is the result of accelerations (e.g., where acceleration refers to either positive acceleration or negative acceleration) of the person's body while running. Traditionally, a GRF for a person running is measured by a direct force measurement system, such as a force plate, an instrumented force treadmill, and/or an insole force sensor. Unfortunately, these traditional direct force measurement systems are expensive and difficult to implement and maintain.

Figure 2:
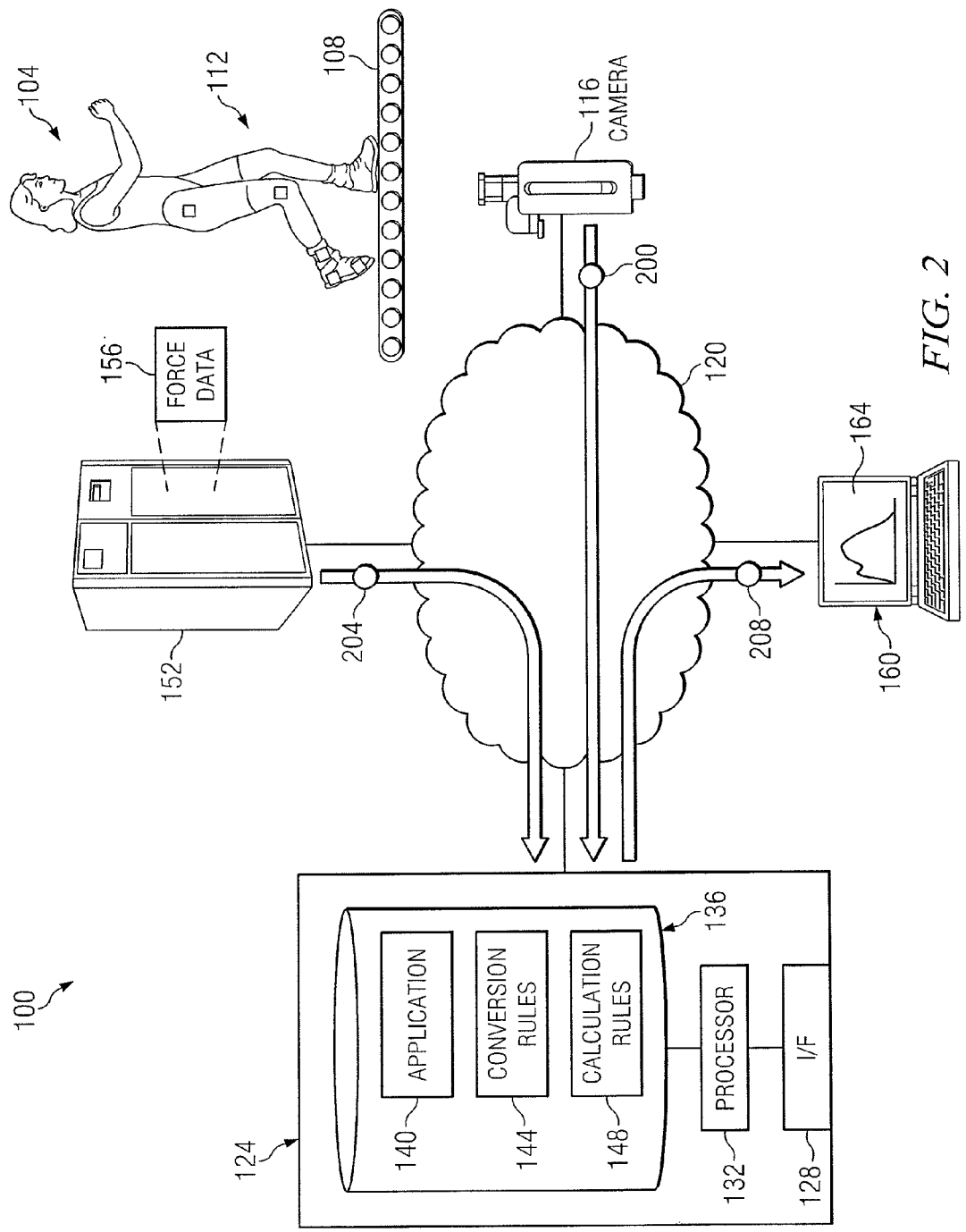
FIG. 2 illustrates a system for predicting a force applied to a surface by a body during a movement.

FIG. 2 illustrates a system 100 for predicting a force applied to a surface by a body during a movement. According to the illustrated embodiment, system 100 includes a calculation device 124 that predicts a force applied to a surface by a body 104 during a movement based at least on the position and/or motion of one or more points of the body 104 during the movement. For example, calculation device 124 may predict the GRF that occurs when a person is running based at least on the position and/or motion of one or more points of the person's body 104 during the run.

As is discussed above, a force applied to a surface by a body during a movement (such as the GRF that occurs when a person is running) is traditionally obtained by expensive direct force measurement systems. In particular embodiments, system 100 of FIG. 2 may provide various advantages over such traditional systems. For example, instead of measuring the force applied to a surface by a body, calculation device 124 may predict the force applied to the surface by the body. This may allow calculation device 124 to determine the force without having to actually measure it. As such, since measuring the force tends to be expensive, in particular embodiments, the force may be determined in a less expensive manner. According to the illustrated embodiment, system 100 includes the body 104, a movement device 108, a plurality of indicators 112, a camera 116, a network 120, the calculation device 124, a storage device 152, and a user output device 160. Body 104 represents any suitable body that may perform a movement. For example, body 104 may be the body of a person, the body of an animal, or any other suitable body that may perform a movement. A movement represents any suitable movement. For example, a movement may refer to running (where running refers to running at any speed or jogging at any speed). A movement may further refer to one or more portions of a movement. For example, a movement may refer to a single step or multiple steps made by a body while running.

Movement device 108 represents any device that allows body 104 to perform a movement. Movement device 108 may be a device that allows body 104 to perform a movement while remaining in substantially the same place. For example, movement device 108 may be a treadmill that allows body 104 to run while remaining substantially in the same place. Movement device 108 may also be any other device that allows body 104 to perform a movement while not remaining in substantially the same place. For example, movement device 108 may be a running surface, such as a track, a street, or any other suitable surface. Indicator 112 represents any suitable indicator used to determine a position and/or motion (e.g., velocity, acceleration, or any other type of motion) of one or more points of body 104 during the movement. Indicator 112 may be a passive indicator (such as reflective tape), an active indicator (such as a sensor that can determine, measure, and/or calculate the position and/or motion of one or more points of body 104 during the movement even if the position and/or motion is not actually measured, such as accelerometers), an inertial system indicator, an electromagnetic indicator, or any other suitable indicator. Indicator 112 may be coupled to body 104 so that it may be used to determine a position and/or motion of one or more points of body 104 during the movement.

System 100 may include any suitable number of indicators 112. For example, system 100 may include five indicators 112 for each leg of body 104, three indicators 112 for each leg of body 104, or any other suitable number of indicators 112 for each leg of body 104. Indicators 112 may be coupled to body 104 in any suitable location of body 104. For example, indicators 112 may be coupled to the joints of a leg of body 104 (such as the hip, knee, and/or ankle of body 104), the heel of body 104, and/or the forefoot of body 104 (such as the ball of the foot of body 104). As such, indicators 112 may allow for the position and/or motion of the body 104's hip, knee, ankle, heel, and/or ball of foot to be determined during the movement. As another example, in an embodiment where only three indicators 112 are used for each leg (or only one leg), indicators 112 may be coupled to the ankle of body 104, the heel of body 104, and the ball of the foot of body 104. As such, indicators 112 may allow for the position and/or motion of the body's ankle, heel, and ball of foot to be determined during the movement.

Although FIG. 2 has been illustrated as including indicators 112 coupled to particular locations of body 104, indicators 112 may be coupled to any suitable positions of body 104. Furthermore, indicators 112 may be coupled directly to body 104 and/or may be coupled to an article of clothing worn on body 104 (such as a shoe). In particular embodiments, indicators 112 may be coupled to body 104 based on one or more measurements. For example, one or more measurements of body 104 may be taken in order to couple a indicator 112 on body 104's hip, knee, ankle, heel and/or ball of foot. In particular embodiments, the position and/or motion of the body 104's hip, knee, ankle, heel and/or ball of foot may be determined even when indicators 112 may be coupled to other locations of body 104. For example, indicators 112 may be coupled to a location near body 104's hip (such as body 104's thigh), and the position and/or motion of body 104's hip may be extrapolated from the position and/or motion of body 104's thigh.

Although FIG. 2 has been illustrated as including indicators 112, in particular embodiments, system 100 may not include indicators 112. For example, indicators 112 may not be needed in order to determine a position and/or motion of one or more points of body 104 during the movement. In such an example, determining the position and/or motion of one or more points of body 104 may include using motion data of body 104 during the movement and further using measurements of body 104. In particular, a pre/post-analysis of body 104 may be used in order to determine joint and segment location of body 104 in order to apply such measurements to motion data during the movement.

Camera 116 represents any component or components that capture motion data of body 104 performing a movement. Camera 116 may be a video camera, a cell phone camera, or any other suitable camera that may capture data of body 104 during the movement. According to the illustrated embodiment, camera 116 may be a high speed video camera that may capture video data of body 104 at every millisecond of the movement. For example, camera 116 may have a high frame rate that allows camera 116 to capture video data of body 104 at every millisecond. In particular embodiments, system 100 of FIG. 2 may further include one or more lighting devices that may provide additional light on body 104 during the movement in order to assist camera 116 in capturing data of body 104 during the movement.

Network 120 represents any network operable to facilitate communication between the components of system 100, such as camera 116, calculation device 124, storage device 152, and user output device 160. Network 120 may be any interconnecting system capable of transmitting audio, video, signals, data, messages, or any combination of the preceding. Network 120 may be all or a portion of a public switched telephone network (PSTN), a public or private data network, a LAN, a MAN, a WAN, a local, regional, or global communication or computer network, such as the Internet, a wireline or wireless network, an enterprise intranet, or any other communication link, including combinations thereof, operable to facilitate communication between the components.

Calculation device 124 represents any component or components that predicts a force applied to a surface by body 104 during a movement. Calculation device 124 may be a network server, any remote server, a mainframe, a host computer, a workstation, a web server, a file server, a personal computer, a laptop, a wireless or cellular telephone, an electronic notebook, a personal digital assistant, or any other device operable to predict a force applied to a surface by body 104 during a movement. The functions of calculation device 124 may be performed by any combination of one or more servers or other components at one or more locations. In the embodiment where the module is a server, the server may be a private server, and the server may be a virtual or physical server. The server may include one or more servers at the same or remote locations. Also calculation device 124 may include any component that functions as a server. In the illustrated embodiment, calculation device 124 includes a network interface 128, a processor 132, and a memory 136.

Network interface 128 represents any device operable to receive information from network 120, transmit information through network 120, perform processing of information, communicate to other devices, or any combination of the preceding. For example, network interface 128 may receive motion data from camera 116. As another example, network interface 128 may communicate the predicted force to user output device 160. Network interface 128 represents any port or connection, real or virtual, including any suitable hardware and/or software, including protocol conversion and data processing capabilities, to communicate through a local area network (LAN), a metropolitan area network (MAN), a wide area network (WAN), or other communication system that allows calculation device 124 to exchange information with network 120, camera 116, storage device 152, user output device 160, or other components of system 100.

Processor 132 communicatively couples to network interface 128 and memory 136, and controls the operation and administration of calculation device 124 by processing information received from network interface 128 and memory 136. Processor 132 includes any hardware and/or software that operates to control and process information. For example, processor 132 executes calculation device management application 140 to control the operation of calculation device 124. Processor 132 may be a programmable logic device, a microcontroller, a microprocessor, any processing device, or any combination of the preceding.

Memory 136 stores, either permanently or temporarily, data, operational software, or other information for processor 132. Memory 136 includes any one or a combination of volatile or non-volatile local or remote devices suitable for storing information. For example, memory 136 may include random access memory (RAM), read only memory (ROM), magnetic storage devices, optical storage devices, or any other information storage device or a combination of these devices. While illustrated as including particular modules, memory 136 may include any information for use in the operation of calculation device 124.

In the illustrated embodiment, memory 136 includes calculation device management application 140, conversions rules 144, and calculation rules 148. Calculation device management application 140 represents any suitable set of instructions, logic, or code embodied in a computer-readable storage medium and operable to facilitate the operation of calculation device 124.

Conversion rules 144 represent any rules regarding converting motion data received from camera 116 to positional data and/or data that represents a motion in order to determine a position and/or motion of one or more points of body 104 during the movement. For example, based on motion data received from camera 116 and conversion rules 144, calculation device 124 may determine a position and/or motion of one or more points of body 104 (such as a position and/or motion of the body 104's hip, knee, ankle, heel, and/or ball of foot during the movement). Conversion rules 144 may include any suitable rule for converting motion data of a movement into positional data and/or data that represents a motion. In particular embodiments, calculation device 124 may receive the already converted positional data and/or data that represents a motion (or the already determined position and/or motion of one or more points of body 104 during the movement). Therefore, in such embodiments, calculation device 124 may not need to utilize conversion rules 144 to convert motion data to positional data and/or data that represents a motion, and/or determine the position and/or motion of one or more points of body 104 during the movement.

Calculation rules 148 represent any rules regarding predicting the force applied to a surface by body 104 during the movement. For example, calculation rules 148 may include one or more rules that may be used to calculate a first curve indicative of a first force between a surface and at least a first portion of the body (such as, in particular embodiments, an acceleration (either positive or negative) of a leg of the body 104 contacting the surface during the movement) and a second curve indicative of a second force between the surface and at least a second portion of the body (such as, in particular embodiments, an acceleration (either positive or negative) of the center of mass of the body 104 during the movement). Furthermore, calculation rules 148 may further include one or more rules that may be used to predict the force applied to the surface by body 104 during the movement. According to the illustrated embodiment, calculation rules 148 may be based, at least in part, on force data 156. Examples of calculation rules 148 are described in further detail below with regard to FIG. 3.

Storage device 152 represents any component or components that store force data 156 for access by one or more components of system 100. Storage device 152 may be a network server, any remote server, a mainframe, a host computer, a workstation, a web server, a file server, a personal computer, a laptop, a wireless or cellular telephone, an electronic notebook, a personal digital assistant, or any other device operable to store force data 156 for access by one or more components of system 100. The functions of storage device 152 may be performed by any combination of one or more servers or other components at one or more locations. In the embodiment where the module is a server, the server may be a private server, and the server may be a virtual or physical server. The server may include one or more servers at the same or remote locations. Also storage device 152 may include any component that functions as a server.

Force data 156 represents any information regarding measured force data for movements. For example, force data 156 may include information regarding the measured force applied to a surface by one or more bodies during one or more movements. In order to assist calculation device 124 in predicting the force applied to the surface by body 104 during a movement, force data 156 may include a collection of measured forces. The measured forces may be forces that were measured while people performed movements similar to the movement for which a prediction is being made and/or for which a prediction may be made in the future. For example, if calculation device 124 is calculating the force applied to the ground by a person running at five meters per second (m/s), force data 156 may include any suitable number of forces measured while any suitable number of people ran at five m/s. The measured forces may have been measured using a traditional direct force measurement system, such as a force plate, an instrumented force treadmill, and/or an insole force sensor. According to the illustrated embodiment, the information in force data 156 may be used by calculation device 124 (or a user of calculation device 124) to modify calculation rules 148. For example, a regression analysis of force data 156 may be used in order to modify calculation rules 148. The modification of calculation rules 148 may cause calculation device 124 to more accurately predict the force applied to a surface, by body 104 during a movement.

User output device 160 represents any component or components that displays information received from calculation device 124. User output device 160 may be a personal computer, a workstation, a laptop, a wireless or cellular telephone, an electronic notebook, a personal digital assistant, or any other device (wireless, wireline, or otherwise) capable of receiving, processing, storing, and/or communicating information with other components of system 100 in order to display information received from calculation device 124. User output device 160 may further allow user to request information from calculation device 124 and/or provide information to calculation device 124. For example, in order to view the predicted force applied to a surface by body 104 during a movement, a user may request the prediction from calculation device 124. User output device 160 may comprise a user interface, such as a display, a microphone, a key pad, or other appropriate terminal equipment usable by a user.

User output device 160 displays a graphical user interface 164 in order to allow a user to view the information provided by calculation device 128. Graphical user interface 164 may be any graphical interface that allows the user to view information provided by calculation device 124, request information from calculation device 124, and/or provide information to calculation device 124. In particular embodiments, graphical user interface 164 may be accessible to a user through a web browser.

In an example embodiment of operation, a user may desire to use calculation device 124 in order to predict a force applied to a surface by a body of a person during a run. In order for this force to be predicted, one or more indicators 112 may be positioned on the body of a person prior to the person running. According to the example embodiment, indicators 112 may be positioned on the hip, knee, ankle, heel, and ball of foot of one leg of the person.

Once the indicators 112 have been placed on the body 104 of the person, the person may begin to run on movement apparatus 108. While the person is running on movement apparatus 108, the person's run may be recorded using camera 116. The motion data recorded by camera 116 of the person's run may then be transmitted to calculation device 124 through network 120 using motion data message 200.

Once calculation device 124 receives the motion data from camera 116, calculation device 124 may determine a position and/or motion of one or more points of the body of the person during the run using conversion rules 144. For example, using conversion rules 144, calculation device 124 may determine the position and/or motion of the person's hip, knee, ankle, heel, and/or ball of foot during one or more steps of the person's run. In particular embodiments, calculation device 124 may calibrate and/or digitize the motion data received from camera 116 in order to determine the position and/or motion of one or more points of the person's body during the run using conversion rules 144.

After the position and/or motion of one or more points of the body of the person is determined for the run, calculation device 124 may calculate a first curve indicative of the acceleration of the leg of the person's body contacting a surface during the run, and may further calculate a second curve indicative of an acceleration of the center of mass of the person's body during the run (as is discussed in greater detail below in conjunction with FIG. 3). According to the example embodiment, such calculations may be performed using calculation rules 148. Calculation rules 148 may include any suitable rule. Examples of calculation rules are described in further detail below with regard to FIG. 3. According to the example embodiment, calculation rules 148 may have been calculated and/or modified based, at least in part, on force data 156. For example, force data 156 may be transmitted to calculation device 124 using force data message 204 in order to be used to calculate and/or modify calculation rules 148. Once the force data 156 is received, calculation device 124 (or a user) may use a regression analysis of force data 156 in order to calculate calculation rules 148.

After the first and the second curves have been calculated using calculation rules 148, calculation device 124 may predict the force applied to the surface by the person's body during the run. For example, based on calculation rules 148, calculation device 124 may predict the force applied to the surface by the person's body during the run by combining the first and second curves. In such an example, the combination may be a summation of the force of each curve at corresponding points of time during the movement. According to the example embodiment, the force predicted by calculation device 124 may include the predicted vertical force on the ground of the person's body, millisecond by millisecond, during the run. Calculation device 124 may then transmit the predicted force to user output device 160 using results message 208.

After receiving results message 208, user output device 160 may display the predicted force applied to the surface by the person's body during the run on graphical user interface 164. As such, a user may be able to view and analyze the predicted force applied to the surface by the person's body during the run without having to actually measure the force using expensive direct force measurement systems. Therefore, in particular embodiments, a user may be able to predict injuries, rehabilitate injuries, detect asymmetric movement styles, enhance training techniques, enhance prosthetic leg design, enhance robot design, and/or enhance shoe design based on the predicted forces millisecond by millisecond.

Although FIG. 2 illustrates calculation device 124, storage device 152, and user output device 160 as separate components, in particular embodiments, two or more of calculation device 124, storage device 152, and/or user output device 160 may be the same device. For example, each of calculation device 124, storage device 152, and user output device 160 may be the same device. As such, the force applied to the surface by a body during a movement may be predicted by the same device that stores force data 156 and displays the predicted force for viewing by a user. Furthermore, although FIG. 2 illustrates user output device 160 as displaying the predicted force, in particular embodiments, calculation device 124 may also include a user interface for displaying the predicted force for viewing by a user.

Furthermore, although FIG. 2 illustrates that calculation device 124 determines the position and/or motion of one or more points of the body during the movement, calculates the first curve and the second curve, and predicts the force applied to the surface by the body during the movement, in particular embodiments, one or more of these determinations, calculations, and predictions may be conducted at a different device than calculation device 124. For example, the determination of the position and/or motion of one or more points of the body during the movement (based on motion data and conversion rules 144) may be conducted at a different device than calculation device 124. As such, once the position and/or motion of one or more points of the body during the movement has been determined by the separate device, information that includes the positions and/or motions may be transmitted to a calculation device 124 so that calculation device 124 may calculate the first and second curves and predict the force applied to the surface by the body during the movement.

Additionally, although FIG. 2 illustrates that motion data is transmitted to calculation device 124 by camera 116, in particular embodiments, positional data and/or data that represents a motion may be transmitted directly from indicators 112 to calculation device 124. As such, the movement of the body may not need to be recorded using camera 116.

Figure 3:
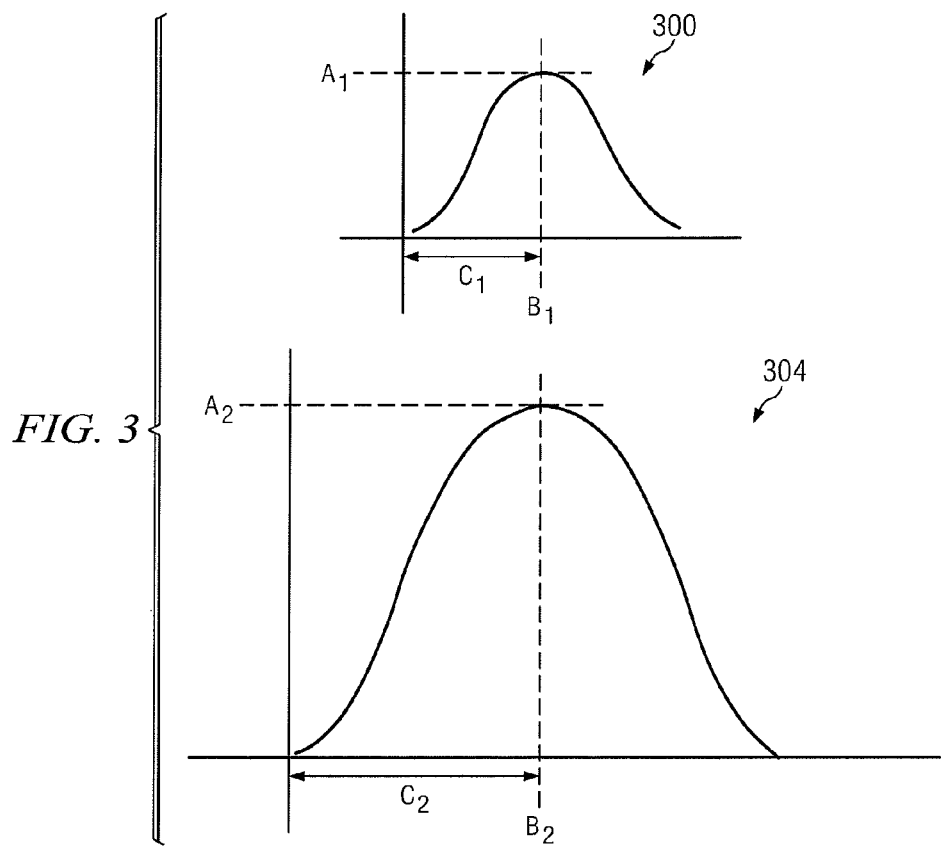
FIG. 3 illustrates a graphical representation of a first curve and a second curve used to predict a force applied to a surface by a body during a movement.

FIG. 3 illustrates a graphical representation of first curve 300 and second curve 304 used to predict a force applied to a surface by a body during a movement. First curve 300 and second curve 304 may be any suitable type of curve. In general, suitable types of curves may include any non-linear curves, such as polynomial curves, trigonometric curves, conic sections, and/or bell-shaped curves. As an example, first curve 300 and second curve 304 may be, without limitation, a bell-shaped curve, such as a Kaiser bell-shaped curve, a Gaussian bell-shaped curve, a Bartlett-Hann bell-shaped curve, a Cosine bell-shaped curve, a Raised Cosine bell-shaped curve, or any other suitable bell-shaped curve. According to the illustrated embodiment, first curve 300 and second curve 304 are Raised Cosine bell-shaped curves.

The teachings of the disclosure recognize that a force applied to a surface by body 104 during a movement (such as when a person is running) consists of at least two different forces: (1) a first force between the surface and at least a first portion of the body (such as, in particular embodiments, an acceleration (either positive or negative) of a leg of the person contacting the surface while the person is running; and (2) a second force between the surface and at least a second portion of the body (such as, in particular embodiments, the force caused by the acceleration (either positive or negative) of the center of mass of the person while running. Since the force applied to the surface by the body 104 during the movement is the result of at least two different forces, in particular embodiments, the force applied to the surface by the body 104 during the movement may be more accurately predicted based on at least two curves that each represent one of these forces, such as first curve 300 and second curve 304 discussed below.

First curve 300 is indicative of an acceleration of a leg of a body contacting a surface during the movement. For example, first curve 300 may be indicative of the force that results from the collision of a person's leg with the ground while the person is running. In particular embodiments, such a collision may be based on impulse-momentum of the leg of the person running.

First curve 300 may be calculated based on a plurality of parameters. For example, according to the illustrated embodiment, first curve 300 may be calculated based on three parameters: $A_1$, $B_1$, and $C_1$. $A_1$ represents the amplitude of first curve 300, $B_1$ represents the center of first curve 300, and $C_1$ represents the width of first curve 300. The value of each of $A_1$, $B_1$, and $C_1$ may be calculated based on the position and/or motion of one or more points of a body during a movement (e.g., it may be based on kinematics). In this example, $A_1$ is a function of an acceleration of a leg of the body during the movement. In particular, with regard to a person who is running, $A_1$ is a function of the average acceleration of the person's leg from the time the leg contacts the ground to the time when the ankle of the leg has a vertical velocity of zero m/s. Furthermore, in this example, $B_1$ and $C_1$ are each a function of the amount of time it takes for a leg of the body to accelerate after contacting the surface during the movement. In particular, with regard to a person who is running, $B_1$ and $C_1$ are each a function of the amount of time from when the person's leg contacts the ground to when the ankle of the leg has a vertical velocity of zero m/s. Example calculation rules 148 for the calculation of $A_1$, $B_1$, and $C_1$ are described in further detail below.

Second curve 304 is indicative of an elastic rebound of a body during a movement. For example, second curve 304 may be indicative of the amount of force due to acceleration of the center of mass of the person while running. In particular embodiments, second curve 304 may be based on the spring system of a person's body while the person is running.

Second curve 304 may be calculated based on a plurality of parameters. For example, according to the illustrated embodiment, second curve 304 may be calculated based on three parameters: $A_2$, $B_2$, and $C_2$. $A_2$ represents the amplitude of second curve 304, $B_2$ represents the center of second curve 304, and $C_2$ represents the width of second curve 304. The value of each of $A_2$, $B_2$, and $C_2$ may be calculated based on the position and/or motion of one or more points of a body during a movement (e.g., it may be based on kinematics). In this example, $A_2$ is a function of the amount of time a leg of the body is in contact with the surface during the movement, and also a function of the amount of time a leg of the body is not in contact with the surface during the movement. In particular, with regard to a person running, $A_2$ is a function of the amount of time the person's leg is in contact with the ground during a step of the run, and also a function of the amount of time the person's leg is not in contact with the ground during a step of the run. Furthermore, in this example, $B_2$ and $C_2$ are each a function of the amount of time a leg of the body is in contact with a surface during a movement. In particular, with regard to a person running, $B_2$ and $C_2$ are each a function of the amount of time the person's leg is in contact with the ground during a step of the run. Furthermore, with regard to a person running, $B_2$ and $C_2$ may be approximately equal to 50% of the time the person's leg is in contact with the ground during a step of the run.

As is discussed above, the parameters of each of the first curve 300 and the second curve 300 may be calculated based on the position and/or motion of one or more points of a body during a movement, and further based on calculation rules 148. According to the illustrated embodiment, with regard to a person running, the calculation rules 148 used to calculate the parameters for first curve 300 and second curve 304 may be independent of the individual running gait of the person or the speed of the person's run. For example, traditionally, a person's run may include at least two factors: (1) a running gait and (2) a running speed. In particular, the running gait of a person may either be a running gait where the person first strikes the ground using a rear portion of their foot or a running gait where the person first strikes the ground using a fore portion of the foot. Furthermore, the speed of a run may be either a speed less than or equal to five m/s or a speed greater than five m/s. According to the illustrated embodiments, despite the fact that people may run with different running gaits and at different speeds, the parameters for first curve 300 and second curve 304 may be calculated for all of the running gaits and speeds based on the following calculation rules 148 that do not depend on the running gait or the speed:

$$A_1 = ((-0.0179 * \text{Average Ankle Acceleration}) + 0.2401) * \text{body weight} \quad (1)$$

where Average Ankle Acceleration represents the average acceleration of the person's leg from the time the leg contacts the ground to the time when the ankle of the leg has a vertical velocity of zero m/s $$B_1 \text{ and } C_1 = (0.8744 * \text{Time to Ankle } Vz=0) + 3.5791 \quad (2)$$

where Time to Ankle Vz=0 represents the amount of time (milliseconds) from when the person's leg contacts the ground to when the ankle of the leg has a vertical velocity of zero m/s $$A_2 = ((1.2855 * ((Tc+Tair)/Tc)) + 0.5329) * \text{body weight} \quad (3)$$

where Tc represents an amount of time (milliseconds) the person's leg is in contact with the ground during a step of the run where Tair represents an amount of time (milliseconds) the person's leg is not in contact with the ground during a step of the run.

$$B_2 = (0.4598 * Tc) + 6.4547 \quad (4)$$

where Tc represents an amount of time (milliseconds) the person's leg is in contact with the ground during a step of the run $$C_2 = (0.5673 * Tc) - 3.0838 \quad (5)$$

where Tc represents an amount of time (milliseconds) the person's leg is in contact with the ground during a step of the run Although FIG. 3 has been illustrated as calculating first curve 300 and second curve 304 using the calculation rules 148 that do not depend on running gait or speed, in particular embodiments, first curve 300 and second curve 304 may be calculated using different calculation rules 148 for each running gait and each running speed. As a first example, when a person is running at a speed less than or equal to five m/s, and one of the steps of the person during the run results in a rear portion of the person's foot striking the ground first, the following calculation rules 148 may be used to calculate the parameters for first curve 300 and second curve 304 for that step:

$$A_1=((-0.0176*\text{Average Ankle Acceleration})+0.2839)*\text{body weight} \quad (6)$$

where Average Ankle Acceleration represents the average acceleration of the person's leg from the time the leg contacts the ground to the time when the ankle of the leg has a vertical velocity of zero m/s $$B_1 \text{ and } C_1=(0.6424*\text{Time to Ankle } Vz=0)+9.1173 \quad (7)$$

where Time to Ankle Vz=0 represents the amount of time (milliseconds) from when the person's leg contacts the ground to when the ankle of the leg has a vertical velocity of zero m/s $$A_2=((1.3549*((Tc+Tair)/Tc))+0.4303)*\text{body weight} \quad (8)$$

where Tc represents an amount of time (milliseconds) the person's leg is in contact with the ground during a step of the run
where Tair represents an amount of time (milliseconds) the person's leg is not in contact with the ground during a step of the run.

$$B_2=(0.4402*Tc)+9.5265 \quad (9)$$

where Tc represents an amount of time (milliseconds) the person's leg is in contact with the ground during a step of the run $$C_2=(0.5362*Tc)+4.2730 \quad (10)$$

where Tc represents an amount of time (milliseconds) the person's leg is in contact with the ground during a step of the run As a second example, when a person is running at a speed less than or equal to five m/s, and one of the steps of the person during the run results in a fore portion of the person's foot striking the ground first, the following calculation rules 148 may be used to calculate the parameters for first curve 300 and second curve 304 for that step:

$$A_1=((-0.0174*\text{Average Ankle Acceleration})+0.2340)*\text{body weight} \quad (11)$$

where Average Ankle Acceleration represents the average acceleration of the person's leg from the time the leg contacts the ground to the time when the ankle of the leg has a vertical velocity of zero m/s $$B_1 \text{ and } C_1=(0.8395*\text{Time to Ankle } Vz=0)+6.1482 \quad (12)$$

where Time to Ankle Vz=0 represents the amount of time (milliseconds) from when the person's leg contacts the ground to when the ankle of the leg has a vertical velocity of zero m/s $$A_2=((1.4268*((Tc+Tair)/Tc))+0.3699)*\text{body weight} \quad (13)$$

where Tc represents an amount of time (milliseconds) the person's leg is in contact with the ground during a step of the run
where Tair represents an amount of time (milliseconds) the person's leg is not in contact with the ground during a step of the run $$B_2=(0.5049*Tc)-1.1488 \quad (14)$$

where Tc represents an amount of time (milliseconds) the person's leg is in contact with the ground during a step of the run $$C_2=(0.5703*Tc)-4.6535 \quad (15)$$

where Tc represents an amount of time (milliseconds) the person's leg is in contact with the ground during a step of the run As a third example, when a person is running at a speed greater than five m/s, and one of the steps of the person during the run results in a rear portion of the person's foot striking the ground first, the following calculation rules 148 may be used to calculate the parameters for first curve 300 and second curve 304 for that step:

$$A_1=((-0.0169*\text{Average Ankle Acceleration})+0.3759)*\text{body weight} \quad (16)$$

where Average Ankle Acceleration represents the average acceleration of the person's leg from the time the leg contacts the ground to the time when the ankle of the leg has a vertical velocity of zero m/s $$B_1 \text{ and } C_1=(0.9495*\text{Time to Ankle } Vz=0)+2.8428 \quad (17)$$

where Time to Ankle Vz=0 represents the amount of time (milliseconds) from when the person's leg contacts the ground to when the ankle of the leg has a vertical velocity of zero m/s $$A_2=((1.5066*((Tc+Tair)/Tc))+0.0005)*\text{body weight} \quad (18)$$

where Tc represents an amount of time (milliseconds) the person's leg is in contact with the ground during a step of the run
where Tair represents an amount of time (milliseconds) the person's leg is not in contact with the ground during a step of the run.

$$B_2=(0.4767*Tc)+4.0482 \quad (19)$$

where Tc represents an amount of time (milliseconds) the person's leg is in contact with the ground during a step of the run $$C_2=(0.5640*Tc)-0.2393 \quad (20)$$

where Tc represents an amount of time (milliseconds) the person's leg is in contact with the ground during a step of the run As a fourth example, when a person is running at a speed greater than five m/s, and one of the steps of the person during the run results in a fore portion of the person's foot striking the ground first, the following calculation rules 148 may be used to calculate the parameters for first curve 300 and second curve 304 for that step:

$$A_1=((-0.0177*\text{Average Ankle Acceleration})+0.2318)*\text{body weight} \quad (21)$$

where Average Ankle Acceleration represents the average acceleration of the person's leg from the time the leg contacts the ground to the time when the ankle of the leg has a vertical velocity of zero m/s $$B_1 \text{ and } C_1=(0.5966*\text{Time to Ankle } Vz=0)+10.7019 \quad (22)$$

where Time to Ankle Vz=0 represents the amount of time (milliseconds) from when the person's leg contacts the ground to when the ankle of the leg has a vertical velocity of zero m/s $$A_2 = ((1.2692*((Tc+Tair)/Tc))+0.5575)*\text{body weight} \tag{23}$$

where Tc represents an amount of time (milliseconds) the person's leg is in contact with the ground during a step of the run where Tair represents an amount of time (milliseconds) the person's leg is not in contact with the ground during a step of the run $$B_2 = (0.5571*Tc) - 4.6718 \tag{24}$$

where Tc represents an amount of time (milliseconds) the person's leg is in contact with the ground during a step of the run $$C_2 = (0.5821*Tc) - 5.7241 \tag{25}$$

where Tc represents an amount of time (milliseconds) the person's leg is in contact with the ground during a step of the run Although FIG. 3 has been described above as utilizing particular calculation rules 148 in order to calculate the parameters for first curve 300 and second curve 304, in particular embodiments, any suitable calculation rules 148 for calculating the parameters for first curve 300 and second curve 304 may be used. For example, as is discussed above with regard to FIG. 2, system 100 may include force data 156. Such force data 156 may be used to modify one or more of these calculation rules 148. In particular, as is discussed above with regard to FIG. 2, force data 156 may include measured force data for one or more people performing one or more movements. The measured forces may be forces that were measured while people performed movements similar to the movement for which a prediction is being made or for which a prediction may be made in the future. Therefore, if calculation device 124 is calculating the force applied to the ground by a person running at five meters per second (m/s), force data 156 may include any suitable number of forces measured while any suitable number of people ran at five m/s. The information in force data 156 may be used by calculation device 124 (or a user of calculation device 124) to calculate and/or modify calculation rules 148. For example, one or more of the above calculation rules 148 may be calculated and/or modified based on a best fit statistical modeling approach using a regression analysis of force data 156. As such, not only may the force applied to the surface by body 104 during a movement be derived from kinematics, but in particular embodiments, it may also be derived from calculation rules 148 that are derived from a regression analysis of force data 156. In particular, such regression analysis may be used to calculate and/or modify the calculation rules 148 so as to provide more accurate values for $A_1, B_1, C_1, A_2, B_2$, and $C_2$, as would be understood by one of ordinary skill in the art. Therefore, the calculation and/or modification of such calculation rules 148 may cause calculation device 124 to more accurately predict the force applied to the surface by body 104 during a movement.

In particular embodiments, not only may the calculation rules 148 be modified based on a regression analysis of force data 156, but the calculation rules 148 may be modified based on the number of measured force profiles in force data 156 and/or the number of indicators 112 coupled to body 104. For example, the calculation rules 148 may be modified if one or more measured force profiles are added or removed from force data 156, or if one or more indicators 112 are added to or removed from body 104.

Once each of the parameters of first curve 300 and second curve 304 are calculated, first curve 300 and second curve 304 may be calculated. First curve 300 and second curve 304 may be calculated using any suitable calculation rules 148. For example, according to the illustrated embodiments, first curve 300 and second curve 304 are Raised Cosine bell-shaped curves. As such, in the illustrated embodiment, first curve 300 and second curve 304 may be calculated using the following calculation rules 148 for Raised Cosine bell-shaped curve:

$$Fz_1 = \frac{A_1}{2}\left(1 + \cos\frac{t - B_1}{C_1}\pi\right) \tag{26}$$

where $Fz_1$ represents the first curve 300

$$Fz_2 = \frac{A_2}{2}\left(1 + \cos\frac{t - B_2}{C_2}\pi\right) \tag{27}$$

where $Fz_2$ represents the second curve 304

Although FIG. 3 has been described above as utilizing particular calculation rules 148 in order to calculate first curve 300 and second curve 304, in particular embodiments, any other calculation rules 148 may be used to calculate first curve 300 and second curve 304. For example, in an embodiment where first curve 300 and second curve 304 are Gaussian bell-shaped curves, the calculation rules 148 used to calculate first curve 300 and second curve 304 may be based on calculation rules 148 for a Gaussian bell-shaped curve.

After the first curve 300 and the second curve 304 have been calculated, calculation device 124 may predict the force applied to the surface by the body during the movement. Calculation device 124 may predict this force by combining first curve 300 and second curve 304. For example, calculation device 124 may predict the force according to the following calculation rule 148:

$$Fz = Fz_1 + Fz_2 \tag{28}$$

where Fz represents the force applied to a surface by the body during the movement at a particular time.

As is discussed above, calculation device 124 may use one or more of the above calculation rules 148 to predict a force applied to the surface by a body during a movement. In particular embodiments, calculation device 124 may use one or more of the above calculation rules 148 to predict a vertical force applied to the surface by a body during a movement, millisecond by millisecond.

Although FIG. 3 has been described above as only including a single curve indicative of an acceleration of a leg of a body contacting a surface during the movement (e.g., first curve 300) and another single curve indicative of an acceleration of the center of mass of a body during a movement (e.g., second curve 304), any number of curves may be utilized to represent each of these two forces, as would be understood by one of ordinary skill in the art. For example, more than one curve may be used to represent the acceleration of the leg of the body contacting the surface during the movement and/or more than one curve may be used to represent the acceleration of the center of mass of the body during the movement.

Figure 4A:
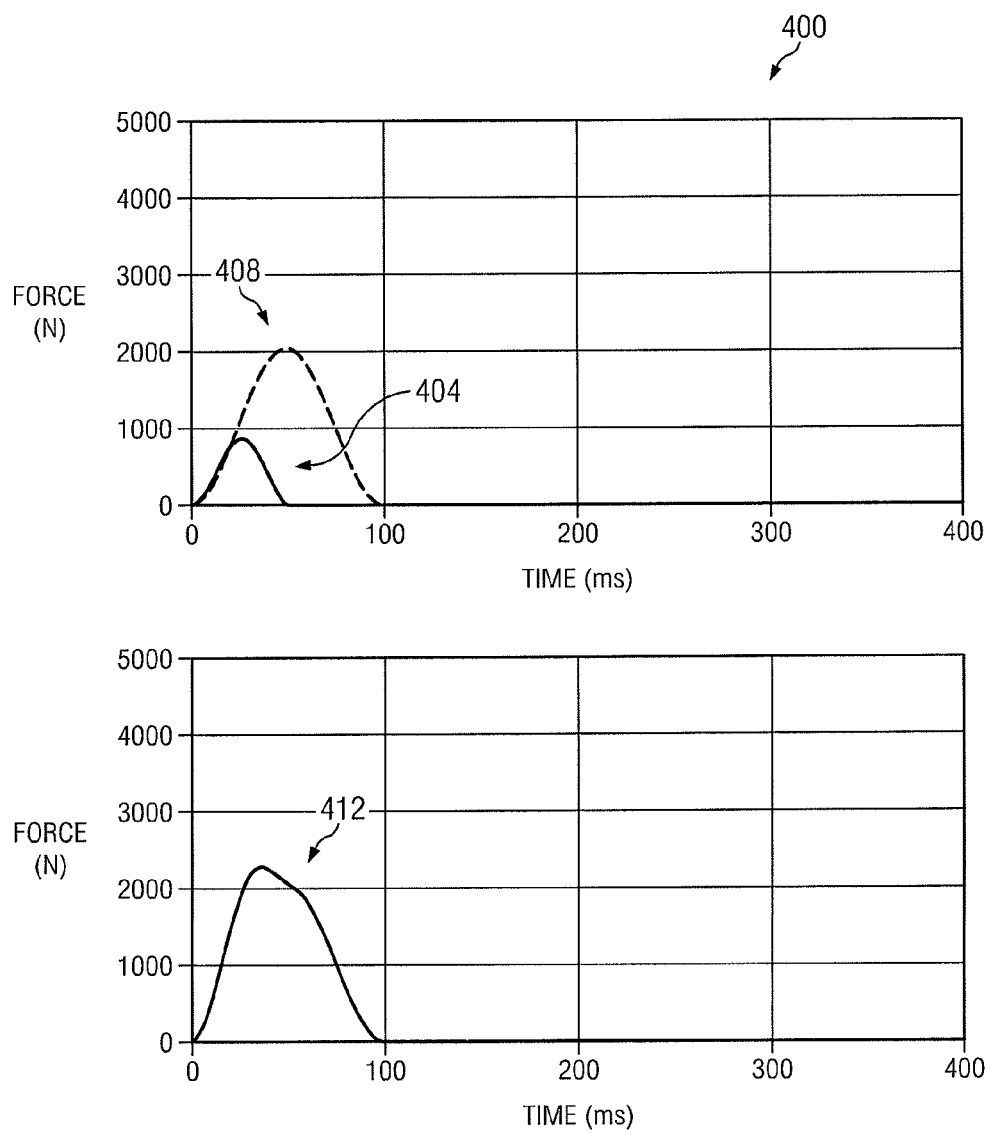
FIGS. 4A-4D illustrate example force profile graphs that may predict a force applied to a surface by a body during a movement.

FIGS. 4A-4D illustrate example force profile graphs that may predict a force applied to a surface by a body during a movement. FIG. 4A includes force profile graphs 400 for a force applied to the ground by a person when the person is running at a speed greater than five m/s, and the person's running gait results in the fore portion of the person's right foot striking the ground first. According to the illustrated embodiment, example force profile graphs 400 include a first curve 404 indicative of the acceleration of the leg of the person contacting the ground during a step of the run, and second curve 408 indicative of the acceleration of the center of mass of the person's body during a step of the run. Furthermore, example force profile graphs 400 further include the predicted force curve 412 of the step of the run. According to the illustrated embodiment, predicted force curve 412 is predicted by combining first curve 404 and second curve 408.

Figure 4B:
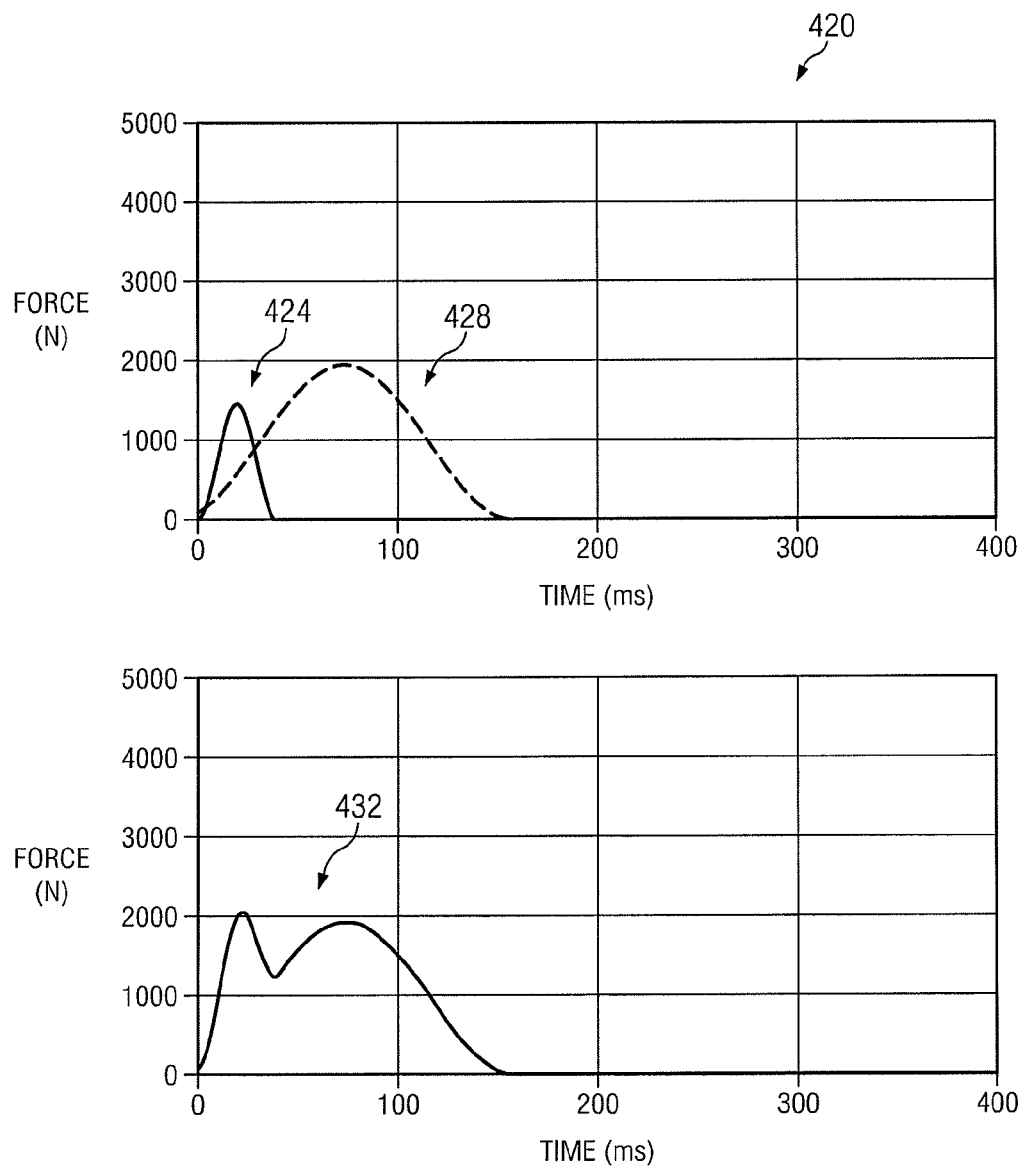

FIG. 4B includes force profile graphs 420 for a force applied to the ground by a person when the person is running at a speed greater than five m/s, and the person's running gait results in the rear portion of the person's right foot striking the ground first. According to the illustrated embodiment, example force profile graphs 420 include a first curve 424 indicative of the acceleration of the leg of the person contacting the ground during a step of the run, and second curve 428 indicative of the acceleration of the center of mass of the person's body during a step of the run. Furthermore, example force profile graphs 420 further include the predicted force curve 432 of the step of the run. According to the illustrated embodiment, predicted force curve 432 is predicted by combining first curve 424 and second curve 428.

Figure 4C:
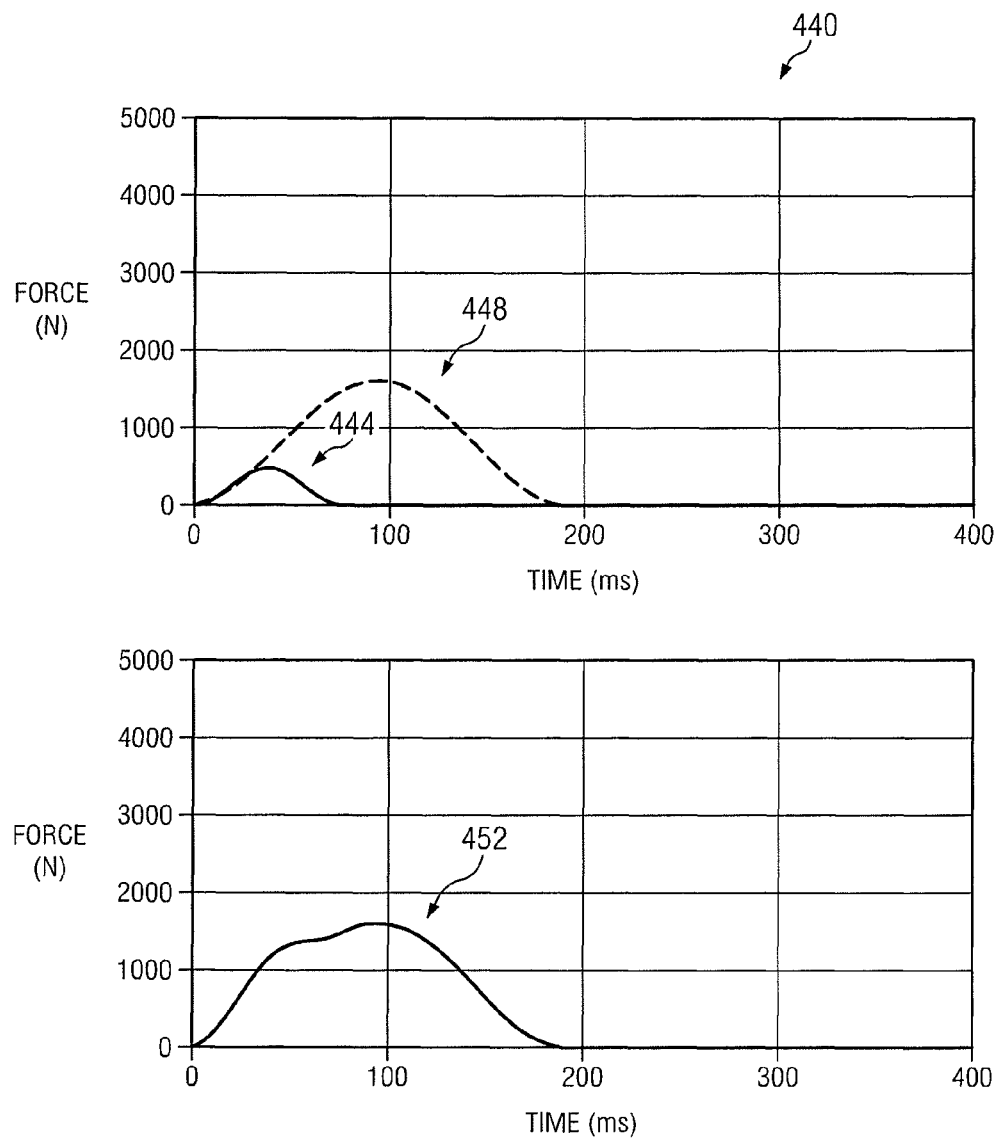

FIG. 4C includes force profile graphs 440 for a force applied to the ground by a person when the person is running at a speed less than or equal to five m/s, and the person's running gait results in the fore portion of the person's right foot striking the ground first. According to the illustrated embodiment, example force profile graphs 440 include a first curve 444 indicative of the acceleration of the leg of the person contacting the ground during a step of the run, and second curve 448 indicative of the acceleration of the center of mass of the person's body during a step of the run. Furthermore, example force profile graphs 440 further include the predicted force curve 452 of the step of the run. According to the illustrated embodiment, predicted force curve 452 is predicted by combining first curve 444 and second curve 448.

Figure 4D:
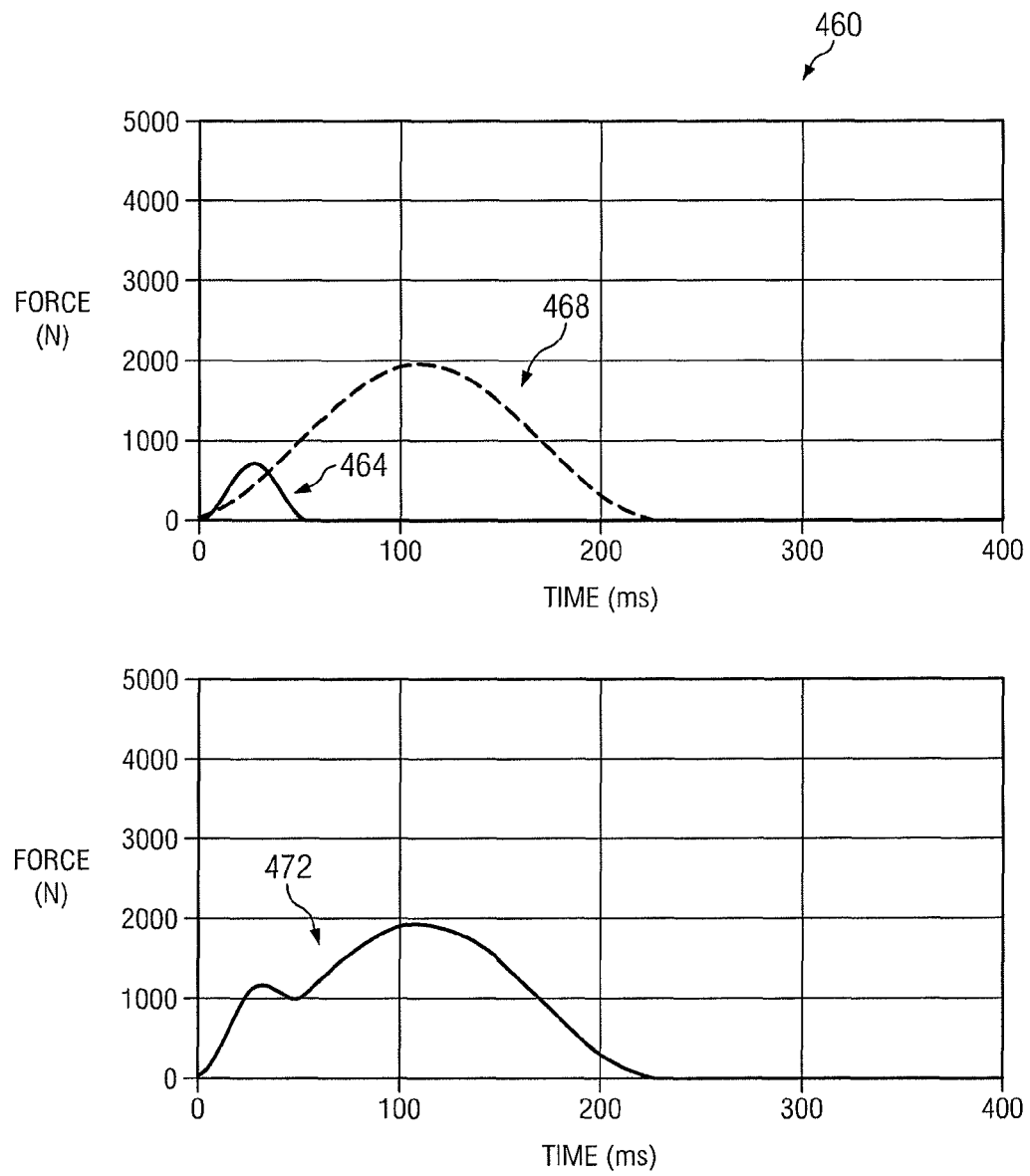

FIG. 4D includes force profile graphs 460 for a force applied to the ground by a person when the person is running at a speed less than or equal to five m/s, and the person's running gait results in the rear portion of the person's right foot striking the ground first. According to the illustrated embodiment, example force profile graphs 460 include a first curve 464 indicative of the acceleration of the leg of the person contacting the ground during a step of the run, and second curve 468 indicative of the acceleration of the center of mass of the person's body during a step of the run. Furthermore, example force profile graphs 460 further include the predicted force curve 472 of the step of the run. According to the illustrated embodiment, predicted force curve 472 is predicted by combining first curve 464 and second curve 468.

Figure 5:
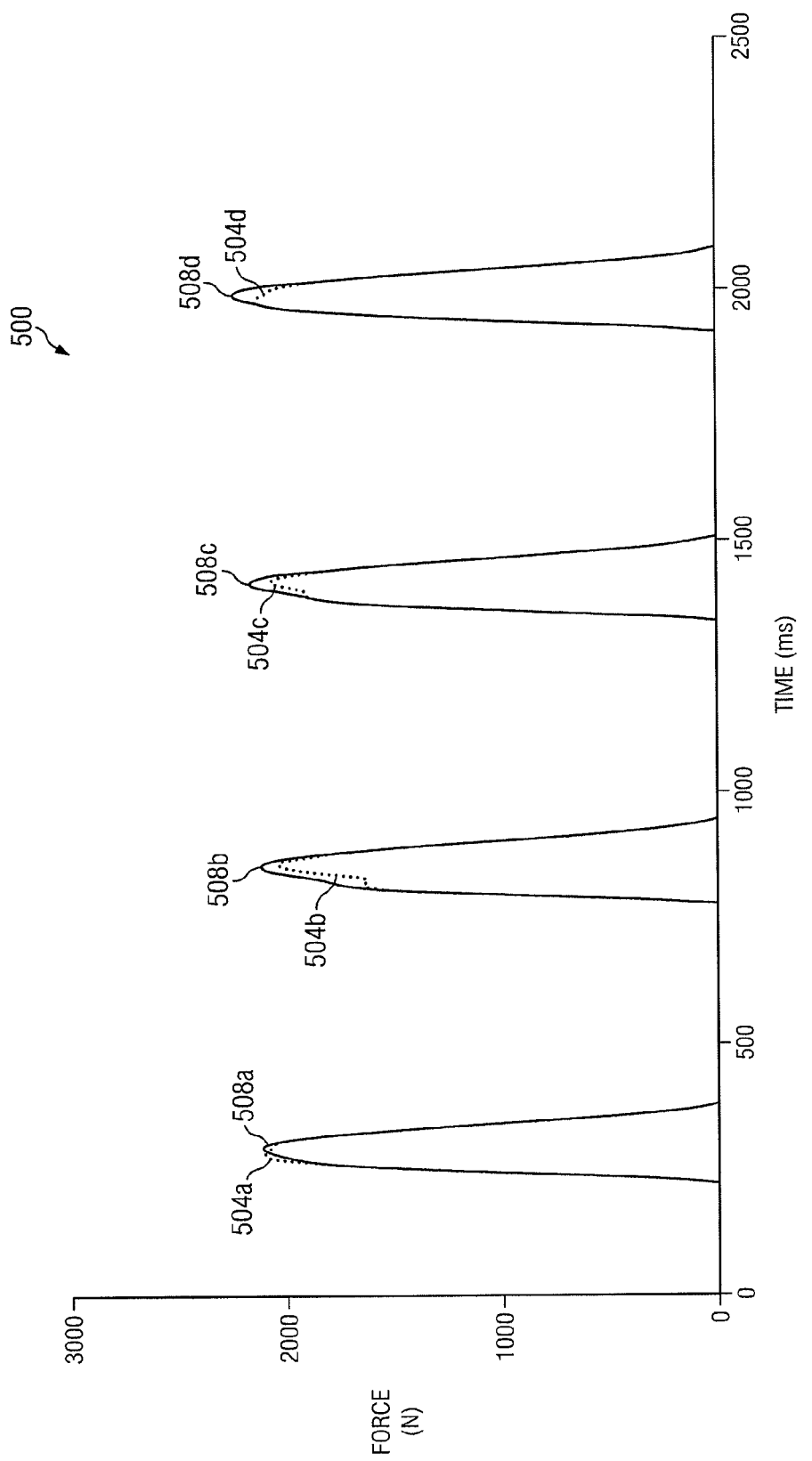
FIG. 5 illustrates example results of a prediction of a force applied to a surface by a body during a movement.

FIG. 5 illustrates example results of the prediction of the force applied to a surface by a body during a movement. According to the illustrated embodiment, example results 500 includes predicted force curves 504 and measured force curves 508. Predicted force curves 504 (which include predicted force curves 504a, 504b, 504d, and 504d) represent the predicted force applied to the ground by a person when the person's right leg is in contact with the ground (while the person is running at a speed of five m/s). Predicted force curves 504 were predicted according to FIGS. 2-4.

Measured force curves 508 (which include measured force curves 508a, 508b, 508c, and 508d) represent the actual measured force applied to the ground by a person when the person's right leg is in contact with the ground (while the person is running at a speed of five m/s). Measured force profiles 508 were measured using an expensive direct force measurement system, such as an instrumented force treadmill.

According to the illustrated embodiment, each of predicted force curves 504 are at least 98% accurate. For example, each of predicted force curves 504 includes a force prediction that is at least 98% similar to the respective measured force curve 508. As such, predicted force curves 504 provide a prediction of the force applied by the person during a movement with at least 98% accuracy.

Although FIG. 5 illustrates example results 500 as including the predicted force applied to the ground by a person when the person's right leg is in contact with the ground (while the person is running at a speed of five m/s), in particular embodiments, example results 500 may include any other suitable results. For example, example results 500 may include the predicted force applied to the ground by a person while the person is running at a speed less than or equal to 5 m/s. As another example, example results 500 may include the predicted force applied to the ground by a person when the person's left leg is in contact with the ground. As a further example, example results may include the predicted force applied to the ground by a person when the person's left leg is in contact with the ground or when the person's right leg is in contact with the ground (while the person is running). In such an example, results for both the left leg and right leg may be predicted when indicators 112 are coupled on both legs of the person.

In particular embodiments, by being able to accurately predict the force applied to a surface by a body during a movement, the systems and methods of the present disclosure may provide various advantages. For example, the force profile curves that may result from such systems and methods may be analyzed to produce a variety of important variables with regard to movements. These variables may include impact forces, loading rates, maximum forces, applied impulses, and/or foot-ground contact times. These variables may be important evaluation tools for orthopedic surgeons, podiatrists, physical therapists, trainers, coaches, and/or designers and/or manufacturers of footwear. Furthermore, these variables may allow a user to predict injuries, rehabilitate injuries, detect asymmetric movement styles, enhance training techniques, enhance prosthetic leg design, enhance robot design, and/or enhance shoe design based on the predicted forces millisecond by millisecond. Furthermore, due to the inexpensive nature of the systems and methods of the present disclosure, such systems and methods may be used in various sites where force profiles curves may have previously been unavailable, such as hospitals, research laboratories, health clubs, athletic facilities, and/or footwear retail stores.

Figure 6:
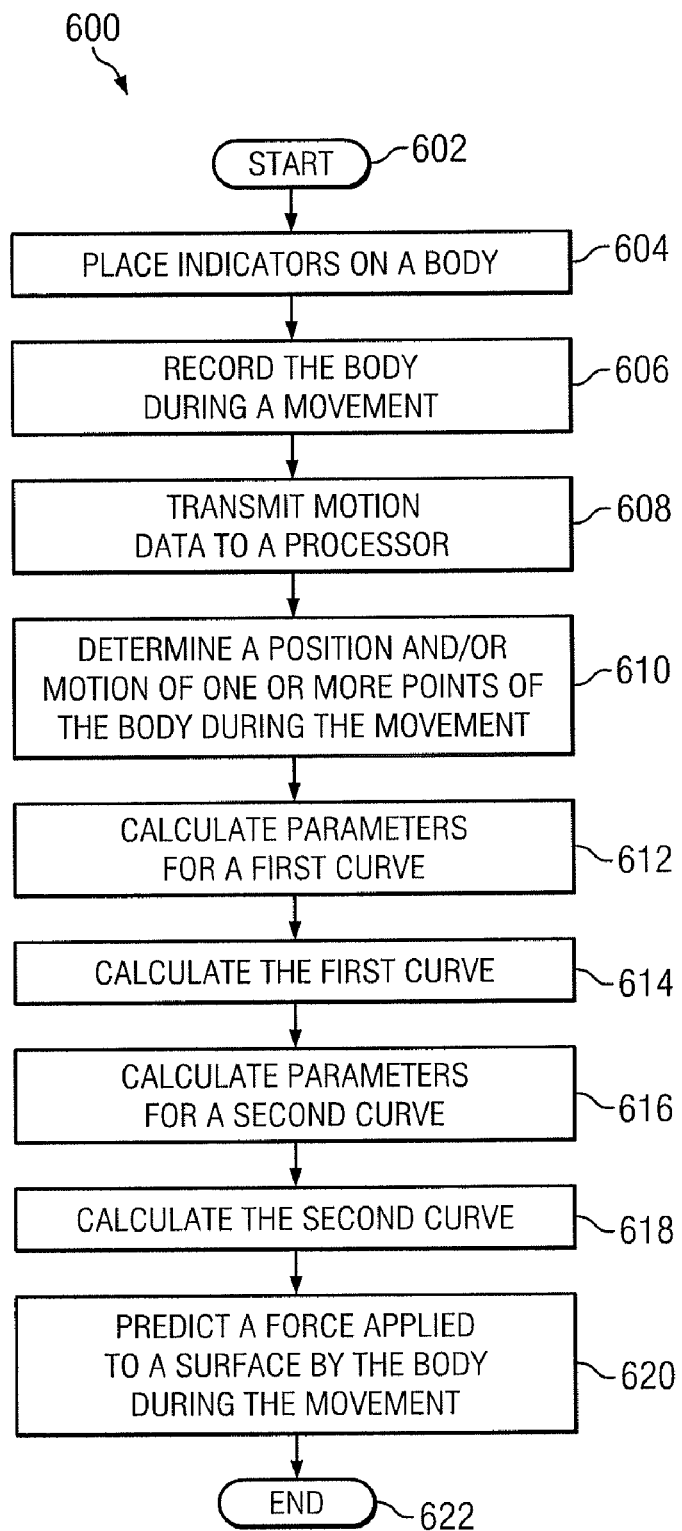
FIG. 6 illustrates a method for predicting a force applied to a surface by a body during a movement.

FIG. 6 illustrates a method 600 for predicting a force applied to a surface by a body during a movement. In particular embodiments, one or more steps of method 600 may be performed by a user of system 100, camera 116, and/or calculation device 124.

The method begins at step 602. At step 604, indicators 112 are placed on a body 104. The indicators 112 may be placed on the hip, knee, ankle, heel, and/or ball of foot of one or more legs of the person. Alternatively, the indicators 112 may be placed on any other locations of the person. Furthermore, in particular embodiments, the method may be conducted without indicators 112.

At step 606, the body is recorded during a movement. For example, camera 116 may be used to record motion data (e.g., such as video data) of a person running. Once the motion data is captured by camera 116, the motion data is transmitted to a processor, at step 608. The motion data may be transmitted to a processor of calculation device 124.

At step 610, a position and/or motion of one or more points of the body during the movement is determined. Calculation device 124 may determine the position and/or motion of one or more points of the body during the movement based on one or more conversion rules 144. In particular embodiments, the position and/or motion of one or more points of the body during the movement may be determined by a different device than calculation device 124. For example, another device (such as another processor) may determine the positions and/or motions and then transmit information that includes the determined positions and/or motions to the calculation device 124.

At step 612, parameters for a first curve are calculated. The parameters may include at least three parameters. The first parameter ($A_1$) may be a function of an acceleration of a leg of the body during the movement. The second parameter ($B_1$) and the third parameter ($C_1$) each may be a function of an amount of time it takes for a leg of the body to accelerate after contacting the surface during the movement. Calculation device 124 may calculate the three parameters using the position and/or motion of one or more points of the body during the movement, and further using one or more calculation rules 148.

At step 614, the first curve is calculated. Calculation device 124 may calculate the first curve using at least the three calculated parameters, and further using one or more calculation rules 148. Alternatively, instead of only a first curve being calculated, any number of curves (such as more than one curve) may be calculated.

At step 616, parameters for a second curve are calculated. The parameters may include at least three additional parameters. The fourth parameter ($A_2$) may be a function of an amount of time a leg of the body is in contact with the surface during the movement, and also a function of an amount of time a leg of the body is not in contact with the surface during the movement. The fifth parameter ($B_2$) and the sixth parameter ($C_2$) may each be a function of the amount of time a leg of the body is in contact with a surface during a movement. Calculation device 124 may calculate the three additional parameters using the position and/or motion of one or more points of the body during the movement, and further using one or more calculation rules 148.

At step 618, the second curve is calculated. Calculation device 124 may calculate the second curve using at least the three additional calculated parameters, and further using one or more calculation rules 148. Alternatively, instead of only a second curve being calculated, any number of curves (such as more than one curve) may be calculated.

At step 620, a force applied to a surface by the body during the movement is predicted. Calculation device 124 may predict the force applied to a surface by the body during the movement using one or more of calculation rules 148. For example, based on one or more of the calculation rules 148, calculation device 124 may predict the force applied to a surface by the body during the movement by combining the first and second curves (or any other number of curves). Once the force applied to a surface by the body during the movement is predicted, the method moves to step 622, where the method ends.

Modifications, additions, or omissions may be made to method 600. For example, although method 600 illustrates the camera 116 as communicating the data used to determine the position and/or motion of one or more points of the body during the movement to calculation device 124, in particular embodiments, the data may be transmitted directly by indicators 112. Additionally, one or more steps in method 600 of FIG. 6 may be performed in parallel or in any suitable order. Furthermore, one or more steps in method 600 of FIG. 6 may be performed at different times and with any amount of time in-between one or more steps. For example, the body's movement may be recorded on a first day, and the force applied by the body during the movement may be predicted substantially instantaneously (e.g., in real-time), the next day, the next week, the next month, or any other amount of time after the recording. Additionally, one or more steps in method 600 of FIG. 6 may be performed in different locations. For example, the body's movement may be recorded in one location, and the force applied by the body during the movement may be predicted in the same location or at any other location.

Although the present invention has been described with several embodiments, a myriad of changes, variations, alterations, transformations, and modifications may be suggested to one skilled in the art, and it is intended that the present invention encompass such changes, variations, alterations, transformations, and modifications as fall within the scope of the appended claims.

What is claimed is:

1. A system comprising:
   at least one memory;
   at least one processor operable to:
      receive video data of a person running;
      based on the video data, determine a position of at least an ankle of a leg of the person, a ball of a foot of the leg of the person, and a heel of the foot of the person during the running;
      based at least on the position of the ankle of the leg of the person, the ball of the foot of the person, and the heel of the foot of the person during the running:
         calculate a first curve indicative of an acceleration of the leg of the person contacting a surface during the running; and
         calculate a second curve indicative of an acceleration of the center of mass of the person during the running; and
      predict a force applied to the surface by the person during the running by combining the first and second curves; and
   a user interface operable to display the predicted force.

2. A system comprising:
   at least one memory; and
   at least one processor operable to:
      receive information that includes a position or motion of one or more points of a body during a movement;
      based at least on the position or motion of the one or more points of the body during the movement:
         calculate a first one or more curves indicative of a first force between a surface and at least a first portion of the body; and
         calculate a second one or more curves indicative of a second force between the surface and at least a second portion of the body; and
      predict a force applied to the surface by the body during the movement by combining the first and second one or more curves.

3. The system of claim 2, wherein the first and second one or more curves comprise bell-shaped curves.

4. The system of claim 2, further comprising at least one user interface operable to display the predicted force.

5. The system of claim 2, wherein the at least one processor is further operable to determine the position or motion of the one or more points of the body during the movement.

6. The system of claim 5, wherein:
a plurality of indicators are coupled to the body during the movement; and
the at least one processor further operable to determine the position or motion of the one or more points of the body during the movement based on the plurality of indicators.

7. The system of claim 2, wherein:
the first one or more curves are calculated based on at least first, second, and third parameters, wherein:
the first parameter of the first one or more curves is a function of an acceleration of the at least a first portion of the body during the movement;
the second parameter and the third parameter of the first one or more curves are a function of an amount of time it takes for the at least a first portion of the body to accelerate after contacting surface during the movement; and
the second one or more curves are calculated based on at least fourth, fifth, and sixth parameters, wherein:
the fourth parameter of the second one or more curves is a function of an amount of time the at least a first portion of the body is in contact with the surface during the movement and an amount of time the at least a first portion of the body is not in contact with the surface during the movement; and
the fifth parameter and the sixth parameter of the second one or more curves are a function of the amount of time the at least a first portion of the body is in contact with the surface during the movement.

8. The system of claim 2, wherein the at least one processor is further operable to predict the vertical force applied to the surface by the body during the movement by combining the first and second one or more curves.

9. The system of claim 2, wherein:
the first one or more curves indicative of the first force between the surface and the at least a first portion of the body comprise first one or more curves indicative of an acceleration of the at least a first portion of the body contacting a surface during the movement; and
the second one or more curves indicative of the second force between the surface and the at least a second portion of the body comprise second one or more curves indicative of an acceleration of the at least a second portion of the body during the movement.

10. A method comprising:
receiving, at one or more processors, information that includes a position or motion of one or more points of a body during a movement;
based at least on the position or motion of the one or more points of the body during the movement:
calculating, at the one or more processors, a first one or more curves indicative of a first force between a surface and at least a first portion of the body; and
calculating, at the one or more processors, a second one or more curves indicative of a second force between the surface and at least a second portion of the body; and
predicting, at the one or more processors, a force applied to the surface by the body during the movement by combining the first and second one or more curves.

11. The method of claim 10, wherein the first and second one or more curves comprise bell-shaped curves.

12. The method of claim 10, further comprising displaying, at a user interface, the predicted force.

13. The method of claim 10, further comprising determining, at the one or more processors, the position or motion of the one or more points of the body during the movement.

14. The method of claim 13, wherein:
a plurality of indicators are coupled to the body during the movement; and
determining, at the one or more processors, the position or motion of the one or more points of the body during the movement comprises determining, at the one or more processors, the position or motion of the one or more points of the body during the movement based on the plurality of indicators.

15. The method of claim 10, wherein:
the first one or more curves are calculated based on at least first, second, and third parameters, wherein:
the first parameter of the first one or more curves is a function of an acceleration of the at least a first portion of the body during the movement;
the second parameter and the third parameter of the first one or more curves are a function of an amount of time it takes for the at least a first portion of the body to accelerate after contacting the surface during the movement; and
the second one or more curves are calculated based on at least fourth, fifth, and sixth parameters, wherein:
the fourth parameter of the second one or more curves is a function of an amount of time the at least a first portion of the body is in contact with the surface during the movement and an amount of time the at least a first portion of the body is not in contact with the surface during the movement; and
the fifth parameter and the sixth parameter of the second one or more curves are a function of the amount of time the at least a first portion of the body is in contact with the surface during the movement.

16. The method of claim 10, wherein predicting, at the one or more processors, the force applied to the surface by the body during the movement by combining the first and second one or more curves comprises predicting, at the one or more processors, the vertical force applied to the surface by the body during the movement by combining the first and second one or more curves.

17. The method of claim 10, wherein:
the first one or more curves indicative of the first force between the surface and the at least a first portion of the body comprise first one or more curves indicative of an acceleration of the at least a first portion of the body contacting a surface during the movement; and
the second one or more curves indicative of the second force between the surface and the at least a second portion of the body comprise second one or more curves indicative of an acceleration of the at least a second portion of the body during the movement.

18. Logic embedded in a computer readable storage medium and operable, when executed by a processor, to:
receive information that includes a position or motion of one or more points of a body during a movement;
based at least on the position or motion of the one or more points of the body during the movement:
calculate a first one or more curves indicative of a first force between a surface and at least a first portion of the body; and
calculate a second one or more curves indicative of a second force between the surface and at least a second portion of the body; and predict a force applied to the surface by the body during the movement by combining the first and second one or more curves.

19. The logic of claim 18, wherein the first and second one or more curves comprise bell-shaped curves.

20. The logic of claim 18, wherein the logic is further operable, when executed by the processor, to display the predicted force at a user interface.

21. The logic of claim 18, wherein the logic is further operable, when executed by the processor, to determine the position or motion of the one or more points of the body during the movement.

22. The logic of claim 21, wherein:
a plurality of indicators are coupled to the body during the movement; and
the logic further operable, when executed by the processor, to determine the position or motion of the one or more points of the body during the movement based on the plurality of indicators.

23. The logic of claim 18, wherein:
the first one or more curves are calculated based on at least first, second, and third parameters, wherein:
the first parameter of the first one or more curves is a function of an acceleration of the at least a first portion of the body during the movement;
the second parameter and the third parameter of the first one or more curves are a function of an amount of time it takes for the at least a first portion of the body to accelerate after contacting the surface during the movement; and the second one or more curves are calculated based on at least fourth, fifth, and sixth parameters, wherein:
the fourth parameter of the second one or more curves is a function of an amount of time the at least a first portion of the body is in contact with the surface during the movement and an amount of time the at least a first portion of the body is not in contact with the surface during the movement; and
the fifth parameter and the sixth parameter of the second one or more curves are a function of the amount of time the at least a first portion of the body is in contact with the surface during the movement.

24. The logic of claim 18, wherein the logic is further operable, when executed by the processor, to predict the vertical force applied to the surface by the body during the movement by combining the first and second one or more curves.

25. The logic of claim 18, wherein:
the first one or more curves indicative of the first force between the surface and the at least a first portion of the body comprise first one or more curves indicative of an acceleration of the at least a first portion of the body contacting a surface during the movement; and
the second one or more curves indicative of the second force between the surface and the at least a second portion of the body comprise second one or more curves indicative of an acceleration of the at least a second portion of the body during the movement.

26. The logic of claim 18, wherein the first portion and the second portion of the body are the same.

* * * * *